(12) United States Patent
Francke

(10) Patent No.: US 6,477,223 B1
(45) Date of Patent: Nov. 5, 2002

(54) TOMOGRAPHIC APPARATUS AND METHOD

(75) Inventor: Tom Francke, Sollentuna (SE)

(73) Assignee: XCounter AB, Danderyd (SE)

( * ) Notice: Subject to any disclaimer, the term of this patent is extended or adjusted under 35 U.S.C. 154(b) by 0 days.

(21) Appl. No.: 09/551,603

(22) Filed: Apr. 17, 2000

(30) Foreign Application Priority Data

Mar. 7, 2000 (SE) .............................. 0000793

(51) Int. Cl.$^7$ ................................ A61B 6/00
(52) U.S. Cl. ........................ 378/19; 378/51; 378/146
(58) Field of Search .................... 378/19, 51, 146; 250/374, 385.1, 385.2, 375, 386, 387

(56) References Cited

U.S. PATENT DOCUMENTS

| | | | | |
|---|---|---|---|---|
| 4,075,491 A | * | 2/1978 | Boyd | 378/19 |
| 4,166,957 A | * | 9/1979 | Jantsch | 250/370.09 |
| 4,253,024 A | * | 2/1981 | Peschmann | 250/374 |
| 4,469,947 A | * | 9/1984 | Allemand et al. | 250/385.1 |
| 4,622,467 A | * | 11/1986 | Britten et al. | 250/389 |
| 4,639,941 A | * | 1/1987 | Hounsfield | 378/11 |
| 4,707,607 A | | 11/1987 | Whetten | |

(List continued on next page.)

FOREIGN PATENT DOCUMENTS

| | | |
|---|---|---|
| DE | 7703944 | 10/1978 |
| JP | 58206996 | 5/1982 |
| JP | 58-206996 | 2/1983 |
| NL | 7703944 | 4/1977 |

Primary Examiner—Robert H. Kim
Assistant Examiner—Chih-Cheng G Kao

(74) Attorney, Agent, or Firm—Birch, Stewart, Kolasch & Birch, LLP

(57) ABSTRACT

A tomographic apparatus for constructing a two-dimensional image of a cut (35) through an object comprises a source (3) for providing a planar beam of radiation so that the beam passes through said object, and thus defines said cut; a detector (9) positioned opposite said source and aligned therewith for detecting the radiation not absorbed or scattered by said object; an arrangement for causing relative movement, between said object and said source and detector combination about an axis of rotation (44) that is perpendicular to said cut through said object; a reconstruction device (39) coupled to said detector for performing a reconstruction process based upon non-absorbed and non-scattered radiation detected by said detector at a plurality of different relative positions between said object and said source and detector combination as reached by said movement causing arrangement, wherein said reconstruction device converts values of non-absorbed and non-scattered radiation into values of absorbed radiation in each of an arbitrarily large number of voxels selected within said cut; and a display (41) coupled to said reconstruction device for projecting a two-dimensional image of said amounts of absorbed radiation. The detector comprises a chamber (13) filled with an ionizable substance, and including a first (17, 18) and a second (27, 29) electrode arrangement, substantially in parallel with each other; a radiation entrance (33) arranged such that the planar radiation beam (1) can enter the chamber between and substantially in parallel with the first and second electrode arrangements and ionize the ionizable substance; an electron avalanche amplification arrangement (15) for avalanche amplification of electrons created during ionization; and a read-out arrangement (27) for detection of the electron avalanches and/or correspondingly produced ions.

17 Claims, 2 Drawing Sheets

U.S. PATENT DOCUMENTS

| | | | |
|---|---|---|---|
| 4,719,354 A | | 1/1988 | Whetten |
| 5,099,846 A | | 3/1992 | Hardy |
| 5,347,130 A | * | 9/1994 | Berthold .................. 250/385.1 |
| 5,391,877 A | | 2/1995 | Marks |
| 5,398,684 A | | 3/1995 | Hardy |
| 5,402,462 A | | 3/1995 | Nobuta |
| 5,414,622 A | | 5/1995 | Walters |
| 5,521,956 A | * | 5/1996 | Charpak ..................... 378/146 |
| 5,614,722 A | * | 3/1997 | Solberg et al. ............. 250/374 |
| 5,644,610 A | * | 7/1997 | Crawford et al. ............. 378/19 |
| 5,959,302 A | * | 9/1999 | Charpak ..................... 250/374 |
| 6,000,739 A | | 12/1999 | Zemit et al. |
| 6,011,265 A | * | 1/2000 | Sauli ......................... 250/374 |
| 6,118,125 A | * | 9/2000 | Carlson et al. .......... 250/385.1 |
| 6,207,958 B1 | * | 3/2001 | Giakos .................... 250/385.1 |
| 6,337,482 B1 | * | 1/2002 | Francke .................. 250/385.1 |
| 6,373,065 B1 | * | 4/2002 | Francke et al. ............. 250/374 |
| 6,385,282 B1 | * | 5/2002 | Francke et al. ............... 378/51 |

* cited by examiner

TOMOGRAPHIC APPARATUS AND METHOD

TECHNICAL FIELD OF THE INVENTION

The present invention generally relates to a tomographic apparatus and method for constructing a two-dimensional image of an object slice from linear projections of ionizing radiation, particularly X-rays, that is transmitted through the slice.

The invention is usable in a variety of fields including medical radiology, computerized tomography (CT), microscopy, and non-destructive testing.

DESCRIPTION OF RELATED ART AND BACKGROUND OF THE INVENTION

It is of great importance in many fields of technology to be capable of constructing a two-dimensional illustrative representation from a series of linear data resulting from various projections (i.e. line-of-sight measurements) taken in the plane of a two-dimensional planar slice or cut of the object one desires to reconstruct. For instance, by employing X-rays to provide a two-dimensional image of a human brain it is commonly known to pass, in the plane of the cut, a planar beam of X-rays through the head and to measure the absorption of X-rays for a number of different directions.

Passing a planar beam of radiation through an object and detecting the amount of absorption within a cut of the object results in a two-dimensional object being projected onto a one-dimensional image. Similarly, passing a planar beam of radiation through an object and detecting the amount of absorption within the object results in a three-dimensional object being projected onto a two-dimensional image. This results inevitably in superimposition of information and resulting loss of the information. Complex techniques have thus to be employed if one wishes to perform an examination with greater sensitivity to spatial variations in radiation absorption and less severe superimposition effects.

In an examination method known as computerized tomography a source of a planar radiation beam and a detector (photographic film or digital detector) are arranged for irradiating the object, e.g. a human head, to be examined by the planar beam, thus defining a thin cut through the object, and for detecting the amount of radiation passed trough (i.e. not absorbed or scattered off) the object. The radiation source and the detector are revolved along a circular or other path around the object in the plane of the planar radiation beam and measurements are performed at several positions, e.g. at every fifth degree of revolution. A two-dimensional reconstruction process of the thin cut of the object is then performed, wherein e.g. brain tissue, bone, liquid-filled cavities, delimited cerebral haemorrhage, if any, etc. become distinguishable as these structures show different absorption. The process may then be repeated for each cut desired to be imaged.

Computerized tomography is described in e.g. U.S. Pat. Nos. 5,414,622; 5,398,684; 5,099,846; 5,391,877; 5,414,622 and 5,402,462.

Means for detecting the radiation in tomographic apparatus of the kind depicted above include X-ray film, various kinds of scintillator-based detectors, solid-state detectors and gaseous detectors. Gaseous detectors are very attractive for this purpose, particularly at lower photon energies. The main advantage of these detectors is that they are cheap to manufacture compared to solid-state detectors, still providing digitized signals.

Tomographic apparatus including gaseous detectors for the detection of X-rays are described in e.g. U.S. Pat. Nos. 4,719,354 and 4,707,607.

Major drawbacks of such tomographic apparatus employing gaseous detectors are, however, the relatively low spatial resolutions that are obtained, and that the sensitivities are somewhat limited due to short ionizations lengths and/or unwanted influences from fluorescent X-ray photons. Further drawbacks include small signal amplitudes and fairly high noise. Also, these tomographic apparatus involves a high dose to the patient.

SUMMARY OF THE INVENTION

Accordingly, it is an object of the present invention to provide a tomographic apparatus and method for constructing a two-dimensional image of an object cut from linear projections of ionizing radiation, particularly X-rays, that is transmitted through said cut, which provide for an improved spatial resolution.

A further object of the invention is to provide such tomographic apparatus and method, which are very sensitive and can thus operate at very low X-ray fluxes.

Still a further object of the present invention is to provide such tomographic apparatus and method, which are effective, fast, accurate, reliable, easy to use, and of low cost.

Yet a further object of the invention is to provide such tomographic apparatus and method, which employ a detector that can be given a length, in the direction of the incoming radiation, for achieving a desired stopping power, which makes it possible to detect a major portion of the incoming radiation.

Still a further object of the invention is to provide such tomographic apparatus and method, which employ any kind of ionizing radiation, including electromagnetic radiation as well as incident particles.

These objects among others are, according to the present invention, attained by a tomographic apparatus and method as claimed in the appended Claims.

In this respect a particular feature of the invention is that it employs a detector, in which electrons released by interactions between photons and the ionizable substance can be extracted in a direction essentially perpendicular to the incident radiation. Hereby it is possible to obtain an improved spatial resolution.

Further, the gap between the electrodes of the detector may be adapted (small enough) to prevent the majority of produced fluorescent X-rays to affect the detected signals, whereby yet a better spatial resolution is obtained.

By employing avalanche amplification of electrons released from ionization (through primary and secondary reactions) in the detector a particularly sensitive tomographic apparatus and method are achieved, which provide for the employment of extremely low doses of radiation, still obtaining signal levels high enough for construction of a two-dimensional image of an object cut exhibiting very low noise levels.

Further characteristics of the invention and advantages thereof will be evident from the following detailed description of preferred embodiments of the invention, which are shown in the accompanying drawings.

BRIEF DESCRIPTION OF THE DRAWINGS

The present invention will become more fully understood from the detailed description of embodiments of the present invention given herein below and the accompanying FIGS. 1–4, which are given by way of illustration only, and thus are not limitative of the invention.

DETAILED DESCRIPTION OF PREFERRED EMBODIMENTS

In the following description, for purposes of explanation and not limitation, specific details are set fourth, such as particular techniques and applications in order to provide a thorough understanding of the present invention. However, it will be apparent to one skilled in the art that the present invention may be practiced in other embodiments that depart from these specific details. In other instances, detailed descriptions of well-known methods and apparatuses are omitted so as not to obscure the description of the present invention with unnecessary details.

Figure 1:
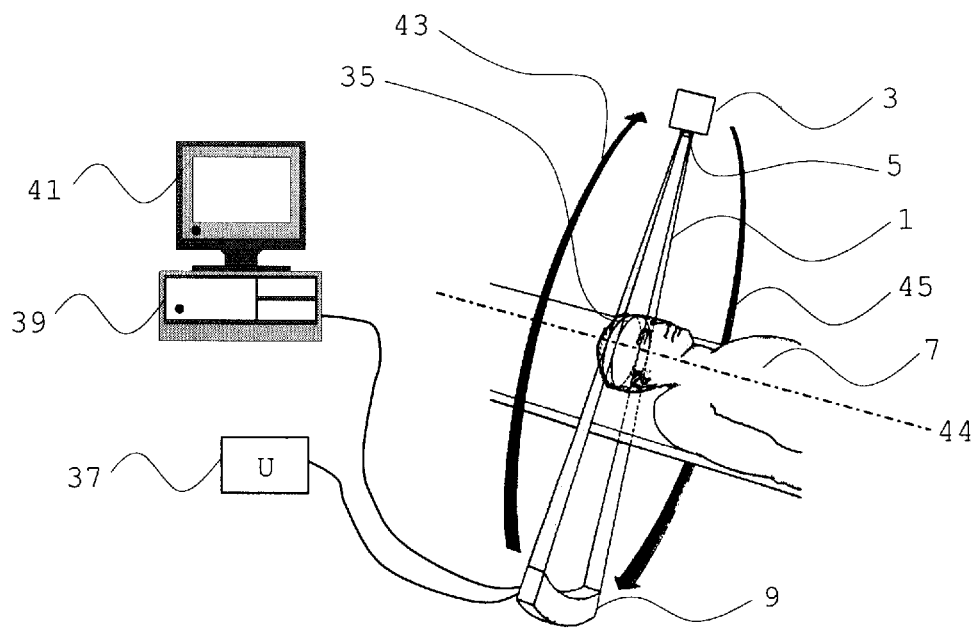
FIG. 1 illustrates schematically a computerized tomography apparatus for medical radiology applications according to an embodiment of the invention.

With reference to FIG. 1, which schematically illustrates a computerized tomography apparatus for medical radiology applications, a preferred embodiment of the present invention will be depicted.

The tomographic apparatus comprises a source 3 of radiation, and a detector 9, lying in the same plane. Source 3 is arranged with a slit 5 or similar in order to provide a planar beam 1 of radiation, which is transmitted through an object 7, such as the head of a human. Thus, planar beam 1 defines a cut or slice 35 through object 7. Cut 35 has a finite but small thickness, typically on the order of a few millimeters, or less, in the case of computerized tomography. Source 3 and detector 9 are aligned and are preferably constructed so as to be always opposite each other; for example, they are each fixedly mounted on a support (not illustrated) which is rotatable in a circular or other path around an axis 44, being orthogonal to the plane of object cut 35, as indicated by arrows 43 and 45. Alternatively, the object may rotate within a motionless source-detector assembly. Alternatively, one detector assembly, which covers the complete 360° arc, could be motionlessly mounted with just the source 3 rotable, or, a plurality of sources may be employed each over a portion of the circle; or else, one 360° source could be employed with energization of only one point of said source at any given time, said point being traversable the entire 360° arc over time.

The rotational force may be provided by a motor, which transmits energy to support gears by means of drive gear (not illustrated in FIG. 1). Detector 9 preferably follows source 3 opposite thereto, and is preferably such that each detection point on the detector is equidistant from the source 3.

Source 3 may be any type of ionizing radiation such as an electron beam in the case of electron microscopy or roentgen or gamma radiation for examining a human, or other body. In the following description, however, the source will be referred to as an X-ray source. The source may be continuous or a pulsed source. Slit 5 shapes the beam of radiation emanating from source 3 into the shape of a fan, preferably at least as wide as object 7, and is typically fabricated of lead, but may be made from any material which absorbs the radiation in unwanted directions.

Detector 9 is an avalanche detector and comprises two electrodes substantially in parallel with each other and an ionization chamber filled with an ionizable substance such as xenon, or a mixture of substances such as xenon and argon, in gas, liquid, or solid phase, see further the detailed description below with reference to FIG. 3. Detector 9 is connected to a power supply 37, and to a electronic processing means, such as a computer 39, which in turn is connected to a display, such as a computer screen 41.

Figure 2:
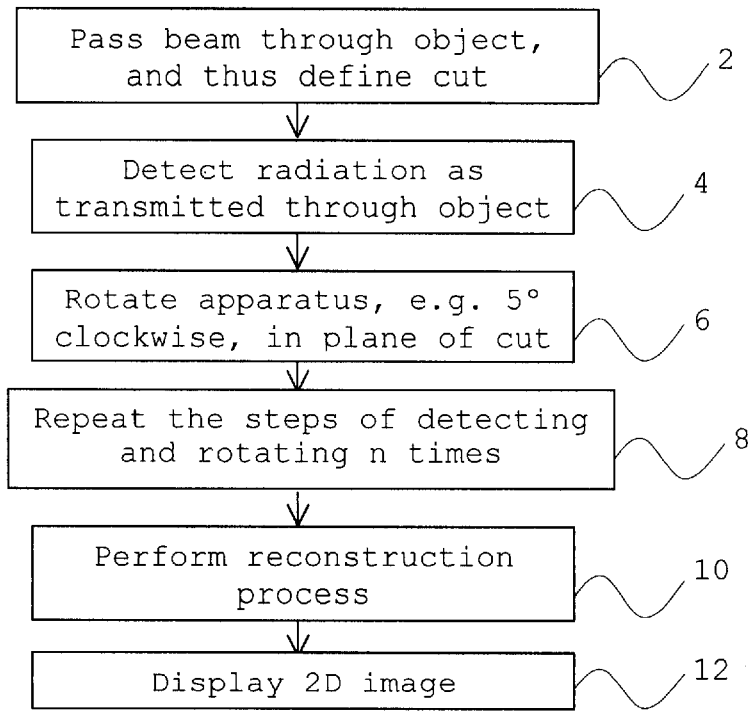
FIG. 2 is a schematic block diagram of an embodiment of the method for constructing a two-dimensional image of an object cut from linear projections of X-rays that is transmitted through the cut.

FIG. 2 is a schematic block diagram of a tomographic method for constructing a two-dimensional image of an object cut from linear projections of radiation that is transmitted through the cut by using the tomographic apparatus of FIG. 1. The tomographic method comprises the following steps.

Planar beam 1 from radiation source 3 is, in a step 2, passed through object 7, which thus defines cut 35. The radiation not absorbed or scattered by said object is, in a step 4, detected by means of detector 9, being positioned opposite source 3 and aligned therewith.

The detector 9 is in this respect arranged such that the planar radiation beam 1 enters the chamber between and substantially in parallel with the two electrodes and ionizes the ionizable substance. Further detector 9 comprises an avalanche amplifying arrangement for avalanche amplifying the electrons created during ionization; and a read-out arrangement, which detects pulses induced by the electron avalanches and/or correspondingly produced ions.

Then, a relative movement between said object and said source and detector combination is in a step 6 caused about an axis of rotation 44 that is perpendicular to cut 35. This movement may be e.g. 1–5°.

Thereafter, in a step 8, the steps of detecting 4 and causing relative movement 6 are repeated a plurality of times. Preferably the number of times, n, which detecting and rotating are repeated, is such that measurement will be performed around the complete 360° arc, or at least a substantial portion thereof. All data is collected and stored in processing means 39.

After, or during the measurement sequences, a reconstruction process is initiated. The process, being performed in a step 10, is based upon non-absorbed and non-scattered (i.e. transmitted) radiation detected by detector 9 at the different rotational positions. The reconstruction process converts values of nonabsorbed and non-scattered radiation into values of absorbed radiation, so called attenuation values, in each of an arbitrarily large number of voxels selected within said cut. The voxels may be thought of as small cubes, which when being arranged in a two-dimensional matrix make up a disc, wherein this disc, during the process, represents the cut of object 7.

The reconstruction process is based on a theoretical mathematical approach developed by J. Radon in 1917, and the basic transforms are now referred to as Radon transforms. More recently, researchers have proposed various methods for object reconstruction, see, for example: A. K. Louis and F. Natterer, "Mathematical Problems of Computerized Tomography," Proceedings of the IEEE, Vol. 71, No.3, pp 379–389 (March 1983); R. M. Lewitt, "Reconstruction Algorithms: Transform Methods,"Proceedings of the IEEE, Vol. 71, No. 3, pp 390–408 (March 1983); Y.

Censor, "Finite Series-Expansion Reconstruction Methods," Proceedings of the IEEE, Vol. 71, No. 3, pp 409–419(March 1983) and C. Jacobson, "Fourier Methods in 3D-Reconstruction from Cone-Beam Data," Ph.D. Dissertation, Dissertation No. 427, Department of Electrical Engineering, Linkoping University, Linkoping, Sweden (1996).

In general, each reconstruction method involves various trade-offs such as image quality (approximations, noise, unsharpness, and artifacts) versus computation time and difficulty of obtaining the required views.

Any of these methods would be applicable in respect of the present invention, and in the following no further comments, as to how the reconstruction process is performed, will be given. The references as indicated above are hereby incorporated by reference.

Finally, in a step 12, a two-dimensional (2D) image of said amounts of absorbed radiation is displayed on display 41, where the image is an X-ray, or other radiation, image of cut 35.

A series of two-dimensional images may be obtained by either taking a succession of images, or else by fabricating an array comprising a plurality of source-detector configurations spaced beside each other e.g., mounted side-by-side on a common support. A further alternative is to perform cone-beam tomography as described in e.g. U.S. Pat. No. 6,000,739, and in references therein, and employ an array of detectors for detection of transmitted portions of said cone beam.

In either case, the output may be portrayed as a three-dimensional picture, for example, by portraying each output element as a shaded or colored translucent ball or cube. Alternatively, a series of transparent light panels may be used for a three-dimensional display.

Figure 3:
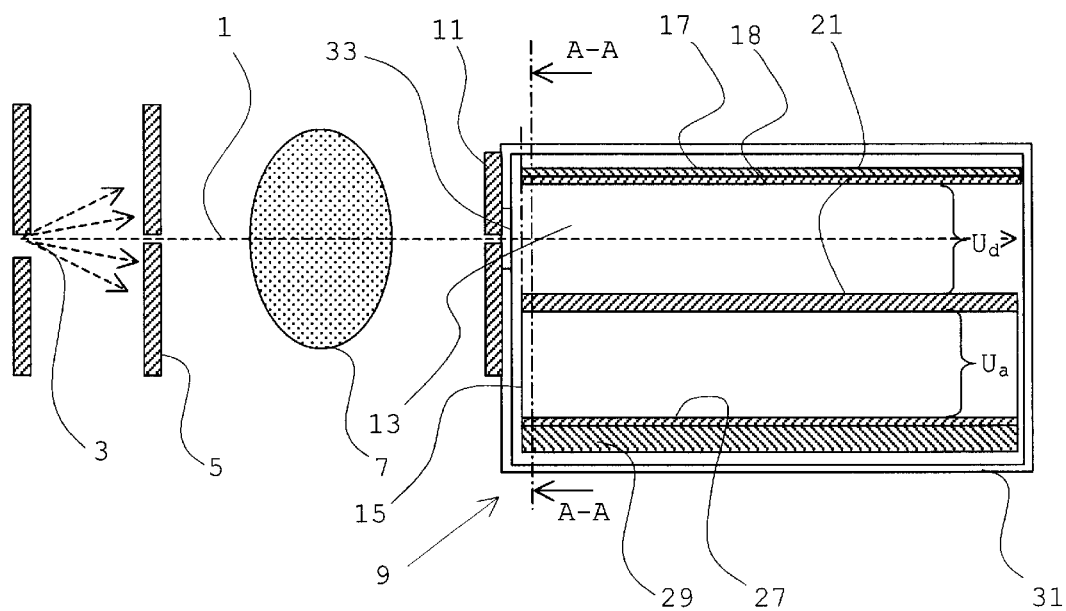
FIG. 3 illustrates schematically, in a cross sectional view, the computerized tomography apparatus of FIG. 1 more in detail.

Next, with reference to FIG. 3, which schematically illustrates, in a sectional view in a plane orthogonal to the plane of planar X-ray beam 1, the computerized tomography apparatus of FIG. 1 more in detail, the detector will be particularly discussed.

The apparatus includes X-ray source 3, which together with collimator window 5, produce the planar fan-shaped X-ray beam 1, for irradiation of the object 7 to be imaged. The collimator window 5 can be replaced by any other arrangement for forming an essentially planar X-ray beam, such as an X-ray diffraction mirror or an X-ray lens etc.

The beam transmitted through the object 7 enters the detector 9. Optionally a slit or collimator window 11, which is aligned with the X-ray beam and forms the entrance for the X-ray beam 1 to the detector 9, is provided. A major fraction of the incident X-ray photons are detected in detector 9, which includes a chamber 13, electrode arrangements 17,18; 21; and 27, 29, respectively. The detector 9 is oriented such that the X-ray beam enters sideways between a first 17, 18 and a second 21 electrode arrangement between which a voltage $U_d$ is applicable. The electrode arrangements are preferably mutually substantially parallel and separated by a short distance, e.g. 10μm–10 mm.

Chamber 13 constitutes a conversion and drift volume and is filled with an ionizable substance. The radiation entered into chamber 13 ionizes the substance and the electrical field created by voltage $U_d$ results in a drift field in region 13 causing drift of electrons towards electrode 21, and thus towards an avalanche amplification region or arrangement 15, and drift of ions towards electrode 17, 18. Chamber 13 is preferably filled with a gas, which can be a mixture of for example 90% krypton and 10% carbon dioxide or a mixture of for example 80% xenon and 20% carbon dioxide. The gas can be under pressure, preferably in a range 1–20 atm. In such instance, the detector includes a gas tight housing 31 with a slit entrance window 33, through which the X-ray beam 1 enters the detector. The window is made of a radiation permeable material.

Detector 9 is arranged such that the released electrons will drift towards and enter an electron avalanche amplification region, preferably through electrode arrangement 21, and wherein they will be multiplied by means of a voltage $U_a$, which may be applied between electrode arrangement 21 and electrode arrangement 27, 29. Voltage $U_a$ is chosen such that electrons from chamber 13 passing electrode 21 is accelerated towards arrangement 27, 29 resulting in electron multiplication and thus multiple avalanche electrons reaching arrangement 27, 29, which also constitutes a read-out arrangement of detector 9 for the detection of pulses induced by the electron avalanches. Alternatively, the read-out arrangement can be formed separated from electrode arrangement 27, 29 (not shown in FIG. 3).

The read-out arrangement 27, 29 is further connected to processing means 39 (only shown in FIG. 1) for the further processing of the detected pulses. The pulses derivable from ionization by different X-ray photons are individually detectable, and hence single-photon detection is realized. Further, the height of a pulse, or the integrated value of a pulse, is proportional to the incident photon energy. Hence, the tomographic apparatus may comprise processing means arranged for discriminating such a pulse in dependence on a pulse derived parameter, preferably pulse height or integrated pulse value. This may be interesting if only X-ray photons of a particular spectral range should be detected and used in the reconstruction process.

The X-ray source 3, the collimator window 5, the optional collimator window 11 and the detector 9 are connected and fixed in relation to each other by a suitable arrangement for example a support (not shown in FIG. 3).

As the X-rays enter the detector in a direction parallel to the electrodes the detector can easily be made with an interaction path long enough to allow a major fraction of the incident X-ray photons to interact and be detected.

Figure 4:
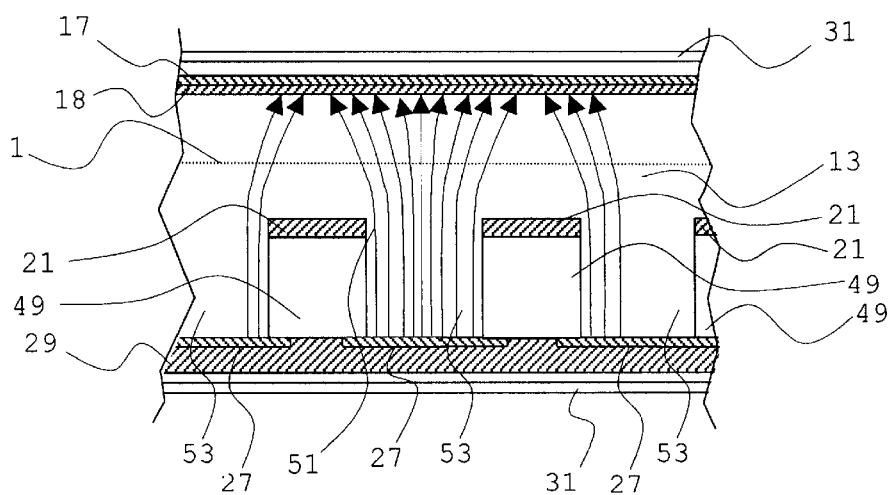
FIG. 4 is a schematic, partly enlarged, cross sectional view, along A—A of FIG. 3.

Referring next to FIG. 4, which shows a schematic, partly enlarged, cross sectional view, taken along A—A of FIG. 3, the detector, will be further described. It shall, however, be appreciated that the present invention is not limited to such a design. For instance, other possible avalanche amplification arrangement designs are further elaborated in our co-pending Swedish patent application No. 9901325-2 entitled Radiation detector, an apparatus for use in planar radiography and a method for detecting ionizing radiation and filed on Apr. 14, 1999, which application hereby is incorporated by reference. It shall also be appreciated that the avalanche amplification arrangement may be a solid-state device or comprise a liquid amplification region.

The first electrode arrangement 17, 18 comprises a dielectric substrate 17 and a conductive layer 18 being a cathode electrode, the second electrode arrangement 21 is also referred to as avalanche cathode, and the third electrode arrangement 27, 29 comprises a dielectric substrate 29 and conductive layer strips 27, being avalanche anode and read-out elements.

A dielectric 49 may be arranged between avalanche cathode 21 and avalanche anode 27. This could be a gas or a solid substrate 49 carrying cathode 21 and anode 27, as shown in FIG. 4. The voltage $U_a$, which is applicable between cathode 21 and anode 27, produces an electric field 51 in a plurality of preferably gas-filled avalanche amplification regions 53. The avalanche regions 53 are formed in a region between and around the edges of the avalanche cathode 21 which are facing each other, and between the avalanche cathode 21 and the avalanche anode 27, where a concentrated electric field will occur due to the applied voltages.

The voltages applied are selected, such that a weaker electric field, drift field, is created over chamber 13, and a stronger field in regions 53. Electrons (primary and secondary electrons) released by interaction in chamber 13 will drift, due to the drift field, towards the avalanche amplification arrangement 15.

They will enter the strong avalanche amplification field and be accelerated. The accelerated electrons will interact with other material (e.g. atoms, molecules etc.) in one of regions 53, causing further electron-ion pairs to be produced. Those produced electrons will also be accelerated in the field, and will interact repetitively with new material, causing further electron-ion pairs to be produced. This process continues during the travel of the electrons in the avalanche region towards anode 27 located at the bottom of the avalanche region, and an electron avalanche is thus formed.

The avalanche regions 53 are formed by openings or channels in cathode 21 and in the dielectric substrate 49, if present. The openings or channels can be of arbitrary shape, e.g. circular or square, as seen from above, or continuous, longitudinal extending between two edges of the substrate 49, if present, and cathode 21. In the case the openings or channels are circular when seen from above they are arranged in rows, each row of openings or channels including a plurality of circular openings or channels. A plurality of longitudinal openings or channels or rows of channels are formed beside each other, parallel with each other or with the incident X-rays. Alternatively, the openings or channels can be arranged in other patterns.

Conductive layer elements 27, which also forms read-out elements, are arranged in connection with the openings or channels forming the avalanche regions 53. Preferably at least one element 27 is provided for each opening or channel. The elements 27 are electrically insulated from each other, and separately connected to the processing means (not shown in FIG. 4).

By providing a plurality of read-out elements 27 as shown in FIG. 4 a detector 9 is achieved, wherein electron avalanches derivable mainly from ionization by transversely separated portions of the planar radiation beam 1 are separately detectable. Hereby, detector 9 provides for one-dimensional imaging. Preferably, the elements are elongated and pointed toward radiation source 3. In such instance elements 27 are preferably put in a fan-shaped arrangement due to divergence of and finite distance to radiation source 3.

In the embodiment described particular locations and geometries of anode, cathode, and read-out arrangements are described. There are, however, a plurality of other locations and geometries that are equally well suitable in connection with the present invention.

It is general for the invention that each incident X-ray photon causes one induced pulse in one (or more) detector electrode element. The pulses are processed in the processing electronics, which eventually shapes the pulses, and integrates or counts the pulses from each pad.

It is also general for the invention that the inter-electrode volumes are thin, which results in a fast removal of ions, which leads to low or no accumulation of space charges. This makes operation at high rate possible. The small distances leads also to low operating voltages, which results in low energy in possible sparks, which is favorable for the electronics. The focusing of the field lines in the avalanche arrangement is also favorable for suppressing streamer formations, which leads to a reduced risk for sparks.

Further, there will in such instance be possible to geometrically discriminate unwanted radiation and electrons, such as fluorescent X-rays and long range electrons, which otherwise would lead to deteriorated spatial resolution and sensitivity. Such detection is further elaborated in our copending Swedish patent applications No. 9901326-0 entitled A method for detecting ionizing radiation, a radiation detector and an apparatus for use in planar beam radiography and filed on Apr. 14, 1999 and No. 0000388-9 entitled Detector and method for detection of ionizing radiation and filed on Feb. 08, 2000. These applications are hereby incorporated by reference.

As an alternative, the electric field in the conversion and drift gap (volume) can be kept high enough to cause electron avalanches, hence to be used in a pre-amplification mode.

As a further alternative, the electrode arrangement 21 may be dispensed with, and an electric field between layer 18 and elements 27 can be kept high enough to cause electron avalanche amplification within the complete volume as defined by regions 13 and 53.

Further, all electrode surfaces may be covered by a resistive material in order to decrease the risk for occurrence of sparks, which will influence the measurement and may destroy electronic equipment of the detector. Such resistive layers are further described in our co-pending Swedish patent application No. 9901327-8 entitled Radiation detector and an apparatus for use in radiography and filed on Apr. 14, 1999. The application is hereby incorporated by reference.

Alternatively, for the same reason, the complete electrodes may be made of a semi-conducting material, e.g. silicon, or only layers 18 and 27 may be of a semi-conducting material.

It will be obvious that the invention may be varied in a plurality of ways. For example, the voltages can be applied in other ways as long as the described electrical fields are created.

Such variations are not to be regarded as a departure from the scope of the invention. All such modifications as would be obvious to one skilled in the art are intended to be included within the scope of the appended Claims.

What is claimed is:

1. A tomographic apparatus for constructing a two-dimensional image of a cut through an object comprising:
   a radiation source for providing a planar beam of radiation so that the beam passes through said object, and thus defines said cut;
   a detector positioned opposite said source and aligned therewith for detecting the radiation not absorbed or scattered by said object;
   an arrangement for causing relative movement, between said object and said source and detector combination about an axis of rotation that is perpendicular to said cut through said object;
   a reconstruction device coupled to said detector for performing a reconstruction process based upon non-absorbed and non-scattered radiation detected by said detector at a plurality of different relative positions between said object and said source and detector combination as reached by said movement causing arrangement, wherein said reconstruction device converts values of non-absorbed and non-scattered radiation into values of absorbed radiation in each of an arbitrarily large number of voxels selected within said cut; and a display coupled to said reconstruction device for projecting a two-dimensional image of said amounts of absorbed radiation;

said detector further comprising:

a chamber filled with an ionizable substance;

a first and a second substantially planar electrode arrangement, located substantially in parallel with each other to at least partially form two oppositely located sidewalls of said chamber;

a radiation entrance arranged such that the planar radiation beam can enter the chamber between and substantially in parallel with the first and second electrode arrangements and ionize the ionizable substance;

an electron avalanche amplification arrangement for avalanche amplification of electrons created during ionization;

a read-out arrangement for detection of the electron avalanches and/or correspondingly produced ions and wherein the electron avalanche amplification arrangement comprises a plurality of avalanche amplification regions and said avalanche amplification arrangement comprises an avalanche cathode arranged between the first and the second electrode arrangement; and wherein a dielectric substrate arranged between the avalanche cathode and the second electrode arrangement such that the avalanche cathode, the dielectric substrate, and the second electrode constitute a laminated structure, the dielectric substrate comprising a plurality of openings or holes aligned with openings or holes of said avalanche cathode, and wherein the read-out arrangement includes a plurality of separated read-out elements, each being adapted to detect electron avalanches, and/or correspondingly produced ions, created in or around a respective one of the plurality of avalanche amplification regions.

2. The apparatus as claimed in claim 1, wherein said arrangement for causing relative movement includes a mechanism for step-wise rotation of said source and detector combination a pre-selected number of steps over a substantial portion of a 360° arc around said axis of rotation.

3. The apparatus as claimed in claim 2, wherein the radiation is pulsed from said radiation source for a short period between each of said rotational steps, so that said source is substantially stationary for the duration of each pulse.

4. The apparatus as claimed in claim 1, wherein radiation from said radiation source is continuous.

5. The apparatus as claimed in claim 1, wherein electron avalanches, and/or correspondingly produced ions, derivable mainly from ionization by transversely separated portions of said planar radiation beam are separately detectable.

6. The apparatus as claimed claim 1, further comprising a signal discriminator arranged for discriminating a pulse derivable from detected electron avalanches, and/or correspondingly produced ions, in dependence on a pulse derived parameter, preferably pulse height or integrated pulse value.

7. The apparatus as claimed in claim 1, wherein the first electrode arrangement includes a dielectric substrate carrying a conductive cathode layer.

8. The apparatus as claimed in claim 7, wherein the second electrode arrangement includes a dielectric substrate carrying a conductive anode layer, the cathode and anode layers are carried on surfaces of the substrates, respectively, which are facing each other.

9. The apparatus as claimed in claim 8, wherein the surfaces of the cathode and anode layers are covered by a resistive material in order to decrease the risk for occurrence of sparks, which will influence the measurement and may destroy electronic equipment of the apparatus.

10. The apparatus as claimed in claim 8, wherein the conductive layers are made of a semiconducting material.

11. The apparatus as claimed in claim 1, wherein the second electrode arrangement comprises a plurality of elongated conductive strips.

12. The apparatus as claimed in claim 1, wherein the read-out arrangement comprises a plurality of elongated conductive strips.

13. The apparatus as claimed in claim 12, wherein each elongated conductive strip is pointing toward the radiation source.

14. The apparatus as claimed in claim 12, wherein the second electrode arrangement and the read-out arrangement are integrated in a single arrangement.

15. The apparatus as claimed in claim 1, wherein the distance between the first and the second electrode arrangement is short enough to discriminate radiation or electrons created, particularly fluorescent X-rays or long range electrons, which otherwise would lead to deteriorated spatial resolution and sensitivity.

16. The apparatus as claimed in claim 1, wherein the electron avalanche amplification arrangement is arranged for electric field concentration.

17. The apparatus as claimed in claim 1, wherein a first voltage is to be applied between the first electrode arrangement and the avalanche cathode and a second voltage is to be applied between the avalanche cathode and the second electrode arrangement, the voltages being selected, such that a weaker electric field, a drift field, is created in chamber between the first electrode arrangement and the avalanche cathode, and a stronger electric field, an avalanche amplification field, is created in the avalanche amplification regions.

* * * * *